(12) United States Patent
Ikeda

(10) Patent No.: US 7,619,060 B2
(45) Date of Patent: Nov. 17, 2009

(54) CYTOPLASMIC POLYHEDROSIS VIRUS PROTEIN COMPLEX OF A POLYHEDRIN AND A VP3 POLYPEPTIDE

(75) Inventor: Keiko Ikeda, Kyoto (JP)

(73) Assignee: Protein Crystal Co., Ltd., Osaka-shi (JP)

( * ) Notice: Subject to any disclaimer, the term of this patent is extended or adjusted under 35 U.S.C. 154(b) by 117 days.

(21) Appl. No.: 10/541,752

(22) PCT Filed: Jan. 7, 2004

(86) PCT No.: PCT/JP2004/000032
§ 371 (c)(1),
(2), (4) Date: Feb. 7, 2006

(87) PCT Pub. No.: WO2004/063371
PCT Pub. Date: Jul. 29, 2004

(65) Prior Publication Data
US 2006/0155114 A1    Jul. 13, 2006

(30) Foreign Application Priority Data
Jan. 10, 2003    (JP)    ............... 2003-005099

(51) Int. Cl.
C07K 14/00    (2006.01)
C12P 21/06    (2006.01)
C12P 21/04    (2006.01)
C12N 7/00     (2006.01)
C12N 5/06     (2006.01)

(52) U.S. Cl. ............ 530/350; 435/69.1; 435/69.7; 435/235.1; 435/348

(58) Field of Classification Search .......... None
See application file for complete search history.

(56) References Cited

U.S. PATENT DOCUMENTS 7,432,347 B2 * 10/2008 Ohta et al. ............ 530/350

FOREIGN PATENT DOCUMENTS

| JP | 2003-155300 | * | 5/2003 |
| WO | WO 95/17425 A | | 6/1995 |
| WO | WO 96/38474 A | | 12/1996 |
| WO | WO 00/04382 A | | 1/2000 |

OTHER PUBLICATIONS

Mori et al., "Immodilization of Bioactive Fibroblast Growth Factor-2 into Cubic Proteinous Microcrystals . . . ", J. Biol. Chem. 282:17289-17296, 2007.*
Hosokawa et al., Materials Research Society, Syposium C, Bio-Inspired Nanoscale Hybrid Systems, Dec. 2002, Abstract C3.5.*
Raw machine English translation of JP 2003-155300, obtained at www.ipdl.inpit.go.jp/homepg_e.ipdl on Dec. 16, 2007.*
Ito et al., "Optical patterning and photochemical fixation of polymer nanoparticles on glass substrates", Appl. Physics Lett. 78:2566-2568, 2001.*
Hajime Mori et al.; "Expression of *Bombyx mori* cytoplasmic polyhedrosis virus polyhedron in insect cells by using a baculovirus expression vector, and its assembly into polyhedra", Journal of General Virology (1993) 74, pp. 99-102.

* cited by examiner

*Primary Examiner*—David J Steadman
(74) *Attorney, Agent, or Firm*—Westerman, Hattori, Daniels & Adrian, LLP

(57) ABSTRACT

It is intended to provide a protein complex and a production process whereby the protein complex can be efficiently produced without lowering its function. It is also intended to provide use of the protein complex in a biosensor, an immobilized enzyme and so on. A protein complex comprising a polyhedral protein having an insect virus encapsulated therein and a target protein having a restricted region of a capsid protein VP3 of cytoplasmic polyhedrosis virus, more specifically, a region which is either a region from the N-terminus to the 40th amino acid residue or a region from the 41st amino acid residue to the 79th amino acid residue as an embedding signal for polyhedron, and a process for producing the same. The polyhedral protein has an effect on improvement in the stability of the target protein, protection thereof or improvement in the preservation properties thereof, or a combination thereof.

8 Claims, 5 Drawing Sheets

Fig. 4

Figure 1:
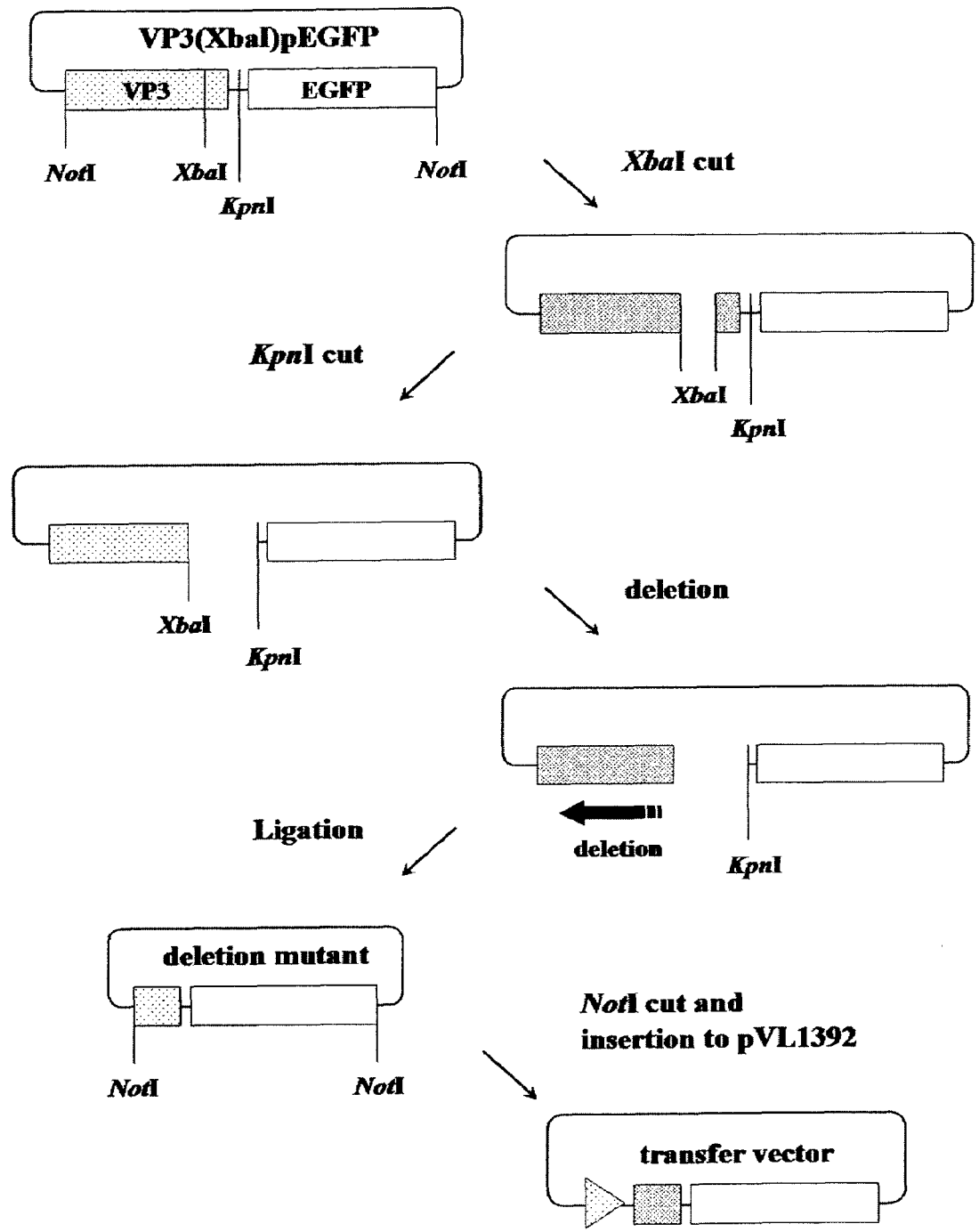

| Shortened VP3 | Number of amino acid residues | Fluorescence intensity |
|---|---|---|
| VP3(1054)/GFP | 347 | 1 |
| VP3(760)/GFP | 249 | 1 |
| VP3(673)/GFP | 220 | 1 |
| VP3(466)/GFP | 151 | 2 |
| VP3(403)/GFP | 130 | 2 |
| VP3(361)/GFP | 116 | 3 |
| VP3(298)/GFP | 95 | 4 |
| VP3(274)/GFP | 87 | 5 |
| VP3(250)/GFP | 79 | 5 |

| Polyhedron | Polyhedron having Cdk5 encapsulated therein |

US 7,619,060 B2

CYTOPLASMIC POLYHEDROSIS VIRUS PROTEIN COMPLEX OF A POLYHEDRIN AND A VP3 POLYPEPTIDE

TECHNICAL FIELD

This invention relates to a protein complex, a process for producing the same, and use of the protein complex in a biosensor, an immobilized enzyme and so on.

BACKGROUND ART

Conventionally, a so-called protein complex, in which a protein is encapsulated in another protein, has been known. As for production of this type of protein complex, for example, a method of applying a solution of a dissolved protein to a surface of a crystalline protein is considered.

However, it is extremely difficult to carry out this method without dissolving the crystalline protein. Accordingly, the fact is that this method is hardly adopted for the purpose of protecting a useful protein (hereinafter referred to as a target protein) such as an enzyme, an antigen, an antibody, a cytokine or a receptor.

As for protection of a target protein, a method of covalently binding a polymer such as a polysaccharide polymer or polyethylene glycol to a target protein has been adopted. This method is a method in which a polymer is bound to a functional group such as an amino group or a carbonyl group in the target protein under mild reaction conditions. However, in this method, the binding site, the catalyzed site or the like of the target protein could not be controlled. In addition, since the binding site, the catalyzed site or the like varies depending on the type of the target protein, the method could not be applied to all the target proteins.

As for preservation of a target protein, generally, a method of preservation at a lower temperature is employed. In addition, a method of adding or mixing a protective substance (e.g., a polysaccharide polymer, polyethylene glycol and the like), which is expected to have a function of stabilizing the protein structure, to or with a target protein is also employed. However, by employing these methods, the stability or the function of the target protein was lost in some cases due to the changes in the environment, which is an external factor. That is, it is because the target protein is easy to dissolve together with the protective substance when water comes in contact, temperature or humidity increases, or dew condensation occurs. In addition, the target protein is degraded or ingested together with the protective substance when putrefactive bacteria such as germs or fungi exist, penetrate, or emerge. Therefore, when the target protein is a polymeric protein such as a protein molecule of some enzymes or antibodies, it lose its function completely by subjecting to a change in even a part of its structure or by degrading a part thereof with the action of a protease. However, when the target protein is used, it is essential that it sufficiently have its function. Therefore, it is necessary to verify the stability of the target proteins in a state of preservation individually. In the case of employing a conventional technique, it is necessary to take the target protein out of the protective substance, therefore, not only it takes a lot of time and efforts, but also the target protein is susceptible to denaturation.

By the way, cytoplasmic polyhedrosis virus forms a polyhedron composed of a polyhedral protein in a cell infected with the virus during the late phase of the viral infection, and many virus particles are embedded in the polyhedron.

The reason why the virus particles enter specifically in this polyhedron is known and it is due to the specific relationship between a capsid protein VP3 of the virus particle and a polyhedral protein (Non-Patent Document 1).

In view of the above-mentioned background, the present inventor completed the invention, which relates to a protein complex contributing to protection, preservation and improvement in stability of a target protein and a process for producing the same, and applied for a patent previously (Patent Document 1). The object of the description of the above-mentioned invention is to embed a polymeric target protein in this polyhedron and to enhance the embedding efficiency. Therefore, by shortening a gene encoding a capsid protein of cytoplasmic polyhedrosis virus, the size (molecular weight) of a protein which can be embedded in a polyhedron is made large, and this target protein is further more efficiently embedded in the polyhedron. Further, as the method, the amino acid sequence of VP3, which is a constituent protein of the envelope of cytoplasmic polyhedrosis virus, is introduced to the N-terminus or the C-terminus of the target protein, and this fusion protein is expressed with a baculovirus vector. At this time, by infecting an insect cell together with a virus expressing a polyhedral protein of cytoplasmic polyhedrosis virus, the fusion protein is embedded in a polyhedron. Accordingly, it is necessary to fuse a cDNA encoding a constituent protein of cytoplasmic polyhedrosis virus and a gene encoding a target protein so that a foreign protein expressed with a baculovirus vector, namely, a target protein is inserted at the N-terminus or the C-terminus of the constituent protein of cytoplasmic polyhedrosis virus. At this time, it is important that the open reading frames encoding the constituent protein and the protein of the target protein gene are cloned in-frame. In this way, a recombinant baculovirus expressing the constituent protein of cytoplasmic polyhedrosis virus and the target protein as one fusion protein is constructed, which is described in the above-mentioned invention.

Patent Document 1: International Patent Application WO 02/36785A1

Non-Patent Document 1: Ikeda et al., (2001) J. Virol. 75, 988-995

Applicants herein incorporate by reference the nucleic acid and amino acid sequences of capsid protein VP3 found in FIG. 1 of Non-Patent Document 1 (Ikeda et al., (2001) J. Virol. 75, 988-995).

DISCLOSURE OF THE INVENTION

The present invention is completed by further improving the above-mentioned invention and identifying VP3, which is used as an embedding signal for polyhedron, within the specific area.

An object of the present invention is to provide a protein complex that can encapsulate a target protein whose size (molecular weight) is increased, in addition a target protein having a fluorescent or light-emitting function or a bioactive function, and moreover a polymeric target protein, and further can verify the function of the target protein in a state of a complex.

In addition, another object of the present invention is to provide a production process that can efficiently produce a protein complex having any of target proteins with a variety of properties encapsulated therein without lowering the function thereof.

Further, another object of the present invention is to provide use of a protein complex in a biosensor, an immobilized enzyme and so on.

A gist of the present invention is a protein complex comprising a polyhedral protein having an insect virus encapsulated therein and a target protein having a restricted region of a capsid protein VP3 of cytoplasmic polyhedrosis virus as an embedding signal for polyhedron.

The restricted region of VP3 is either a region from the N-terminus to the 40th amino acid residue or the region from the 41st amino acid residue to the 79th amino acid residue. In this case, a gist of the present invention is a protein complex comprising a polyhedral protein having an insect virus encapsulated therein and a target protein having, as an embedding signal for polyhedron, a restricted region, which is either a region from the N-terminus to the 40th amino acid residue or a region from the 41st amino acid residue to the 79th amino acid residue of a capsid protein VP3 of cytoplasmic polyhedrosis virus.

The polyhedral protein has an effect on improvement in the stability of the target protein, protection thereof or improvement in the preservation property thereof, or a combination of any of these. In this case, a gist of the present invention is a protein complex comprising a polyhedral protein having an insect virus encapsulated therein and a target protein having, as an embedding signal for polyhedron, a restricted region of a capsid protein of cytoplasmic polyhedrosis virus, more specifically, a restricted region, which is either a region from the N-terminus to the 40th amino acid residue or a region from the 41st amino acid residue to the 79th amino acid residue of VP3, in which the polyhedral protein has an effect on improvement in the stability of the target protein, protection thereof or improvement in the preservation property thereof, or a combination of any of these.

The target protein is at least one member selected from the group consisting of fluorescent or light-emitting proteins, enzymes, antigens, antibodies, cytokines, receptors and bioactive proteins. In this case, a gist of the present invention is a protein complex comprising a polyhedral protein having an insect virus encapsulated therein and a target protein having, as an embedding signal for polyhedron, a restricted region of a capsid protein of cytoplasmic polyhedrosis virus, more specifically, a restricted region, which is either a region from the N-terminus to the 40th amino acid residue or a region from the 41st amino acid residue to the 79th amino acid residue of VP3, and being at least one member selected from the group consisting of fluorescent or light-emitting proteins, enzymes, antigens, antibodies, cytokines, receptors and bioactive proteins, in which the polyhedral protein preferably has an effect on improvement in the stability of the target protein, protection thereof or improvement in the preservation property thereof, or a combination of any of these.

In addition, a gist of the present invention is a process for producing a protein complex, wherein a cell is infected with a vector that has been integrated with a gene encoding a target protein together with a vector that has been integrated with a gene encoding a polyhedral protein, and the cell is cultured, whereby a protein complex having a complex structure composed of the target protein and the polyhedral protein is produced in the cell.

Still further, a gist of the present invention is a biosensor characterized in that a protein complex comprising a polyhedral protein having an insect virus encapsulated therein and a target protein having, as an embedding signal for polyhedron, a restricted region of a capsid protein of cytoplasmic polyhedrosis virus, more specifically, a restricted region, which is either a region from the N-terminus to the 40th amino acid residue or a region from the 41st amino acid residue to the 79th amino acid residue of VP3, and more specifically, being at least one member selected from the group consisting of fluorescent or light-emitting proteins, enzymes, antigens, antibodies, cytokines, receptors and bioactive proteins, in which the polyhedral protein preferably has an effect on improvement in the stability of the target protein, protection thereof or improvement in the preservation property thereof, or a combination of any of these, is arranged in dots or lines on a substrate and immobilized thereon, a biosensor characterized in that the protein complex is packed in such a manner that it can be contacted with a substance in a test solution in a recess formed on a substrate, or a biosensor characterized in that the protein complex is packed in a container in such a manner that it can be contacted with a substance in a test solution.

In addition, a gist of the present invention is an immobilized enzyme in which a protein complex comprising a polyhedral protein having an insect virus encapsulated therein and a target protein having, as an embedding signal for polyhedron, a restricted region of a capsid protein of cytoplasmic polyhedrosis virus, more specifically, a restricted region, which is either a region from the N-terminus to the 40th amino acid residue or a region from the 41st amino acid residue to the 79th amino acid residue of VP3, and more specifically, being at least one member selected from the group consisting of fluorescent or light-emitting proteins, enzymes, antigens, antibodies, cytokines, receptors and bioactive proteins, in which the polyhedral protein preferably has an effect on improvement in the stability of the target protein, protection thereof or improvement in the preservation property thereof, is packed in a container.

BRIEF DESCRIPTION OF THE DRAWINGS

FIG. 1 is a figure illustrating a method of shortening VP3 gene and preparation of a transfer vector.

FIG. 2 is a figure showing the relationship between a shortened VP3 gene and the amino acid residues encoded by the gene.

FIG. 3 shows the determination whether or not a protein encoded by a gene, in which a shortened VP3 gene has been introduced into an EGFP gene, is encapsulated in a polyhedron based on the presence or absence of green fluorescence from the polyhedron.

FIG. 4 shows a green fluorescence intensity observed in a state where EGFP having the nucleotide sequence of a shortened VP3 at the N-terminus is encapsulated in a polyhedron. The fluorescence intensity was graded at five levels, 1+, 2+, 3+, 4+ and 5+.

FIG. 5 shows the results obtained by introducing the region from the 39th amino acid residue to the 79th amino acid residue of VP3 into the N-terminus of Cyclin-dependent kinase 5 as a signal for encapsulation in a polyhedron, thereby encapsulating this protein in a polyhedron, and attaching the polyhedron to a slide glass and performing an antigen-antibody reaction on the surface of the polyhedron.

BEST MODE FOR CARRYING OUT THE INVENTION

A protein complex according to the present invention comprises a target protein having a restricted region of a capsid protein VP3 of cytoplasmic polyhedrosis virus as an embedding signal for polyhedron encapsulated in a polyhedral protein having an insect virus encapsulated therein. Here, "encapsulation" means that it includes a state where a target protein is completely encapsulated in the inside of a polyhedral protein and a state where it is embedded while a part thereof is exposed to the outside of the polyhedral protein. In addition, examples of the shape of the complex include a regular shape such as cube, rectangular parallelepiped and cylinder, and an irregular shape such as a particulate form. According to the shape, the amount of the encapsulated target protein can be increased, the size of the target protein can be increased, or a function such as a bioactive function or a catalytic function can be dramatically enhanced.

In the present invention, the restricted region of VP3 is a region from the 41st amino acid residue to the 79th amino acid residue as well as a region from the N-terminus to the 40th amino acid residue. Incidentally, though it takes time and efforts and is inefficient, a region in which 10 amino acid residues have been added to the N-terminus or the C-terminus of a region from the 41st amino acid residue from the N-terminus to the 79th amino acid residue can also be used.

Figure 2:
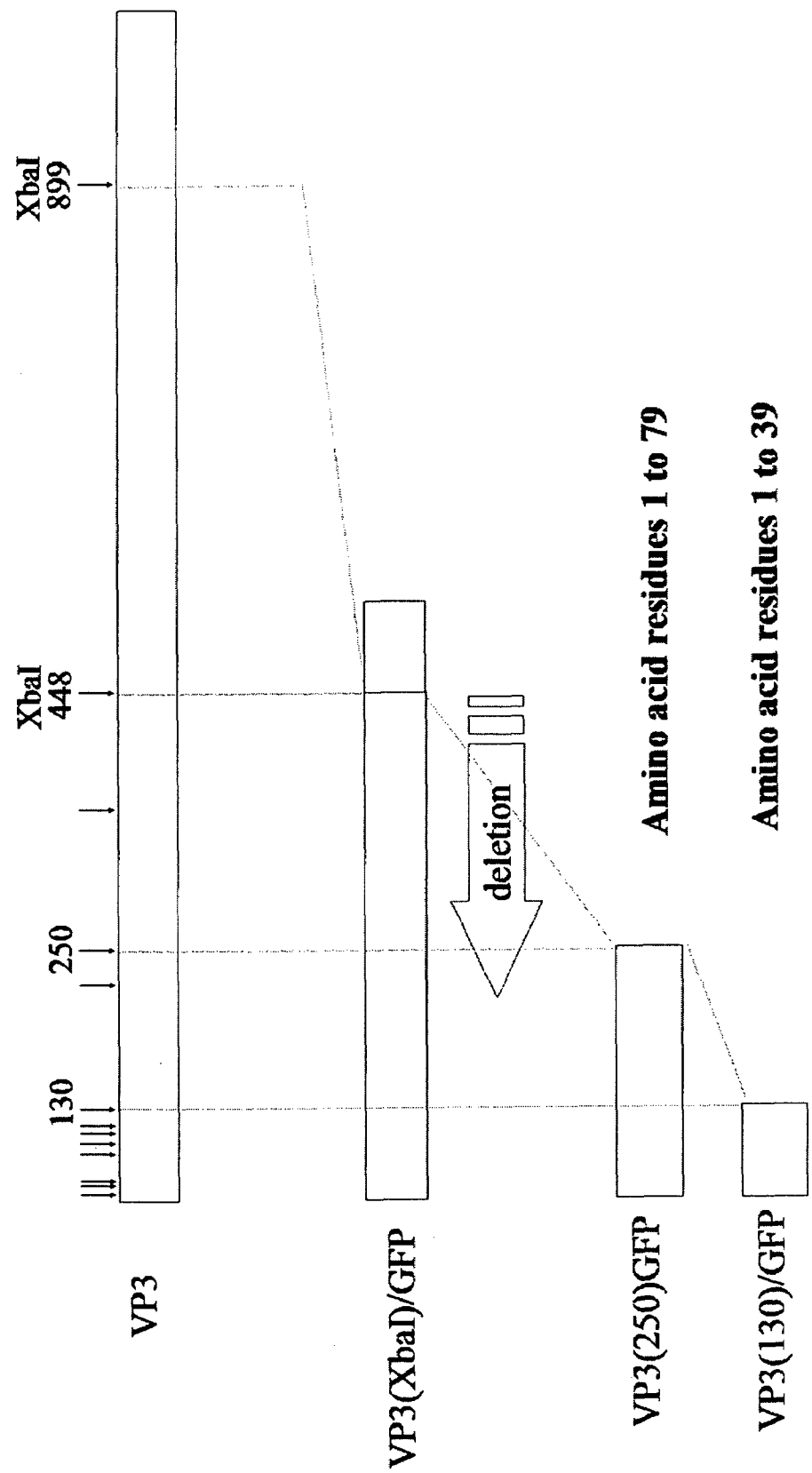

Further, when considering the point of binding to a biologically related chemical substance, the target protein is an enzyme, an antigen, an antibody, a receptor or a cytokine, when considering the point of a photochemical property, it is a light-emitting protein, and when considering the point of an electron transfer reaction, it is a metal-binding protein or a metal ion-containing enzyme. When considering the point of such a property of a target protein, a constitution which is selected from these and is at least one member is preferred.

A process for producing a protein complex according to the present invention comprises introducing a vector that has been integrated with a DNA encoding a target protein having a restricted region of VP3 as a signal simultaneously or together with a vector that has been integrated with a DNA encoding a polyhedral protein into a cell such as an insect cell, an animal cell, a plant cell or an a cellular cell, and culturing the cell under the conditions suitable for each cell. In this way, the protein complex can be efficiently produced without lowering its function. However, the vector that has been integrated with a DNA encoding a target protein and the vector that has been integrated with a DNA encoding a polyhedral protein are a plasmid vector, a virus vector or the like, and it is only necessary to individually select the one suitable for a cell into which a DNA is introduced.

As for use of a protein complex of the present invention, it can be applied as a biosensor such as an immunosensor, a gene sensor or a lipid sensor by arranging and immobilizing the protein complex on a substrate to use the protein complex as a receptor, converting light amount or mass into an electrical signal by a transducer such as SPR, a photon counter or a crystal oscillator, and displaying the electrical signal. As a material for the substrate, a glass, a plastic, a metal or the like can be used. In addition, as a method of bonding the substrate and the protein polyhedron, an adhesive such as gelatin or a macromolecular polymer can be used.

In addition, by using a tubular container, in which a test solution can be passed through, instead of the above-mentioned substrate, and packing the protein complex in the container in such a manner that it can be contacted with a substance in the test solution, it can be applied as a biosensor.

Further, by preparing a particulate protein complex by the same method as in Example 1 using a DNA encoding an enzyme such as a protease, a lipase or an esterase having a catalytic ability, and packing the protein complex in a container in any of various forms, it can be applies as an immobilized enzyme having a catalytic ability.

The detail of the invention of this application will be described with reference to Examples. However, the invention of this application is by no means limited to these Examples.

EXAMPLE 1

The present invention will be described according to Examples and the attached figures to explain it in more detail.

(1) Preparation of a Virus Producing a Polyhedral Protein

In the case where a polyhedron is produced with IPLB-Sf21-AE (Sf21) derived from an insect cell *Spondoptera frugiperda*, to form a cubic polyhedron of *Bombyx mori* cytoplasmic polyhedrosis virus (BmCPV), a recombinant virus (AcCP-H) that had been integrated with a polyhedral protein gene of BmCPV strain H (Mori et al., (1993) J. Gen. Virol. 74, 99-102) was inoculated. This AcCP-H is a recombinant virus that has been integrated with a polyhedral protein gene of strain H at the downstream of the polyhedrin promoter of a baculovirus vector derived from *Autographa californica* nucleopolyhedrovirus (AcNPV).

(2) Analysis of a Signal Composed of Only a Restricted Region of a Capsid Protein VP3

1) Shortening of BmCPV S4 Encoding a Capsid Protein VP3

A plasmid pVP3(XbaI)EGFP (International Patent Application WO 02/36785A1) was digested with a restriction enzyme XbaI, and further digested with a restriction enzyme KpnI. This DNA was dissolved in 100 μl of ExoIII buffer in a tube, and 1 μl of Exonuclease III was added, stirred and incubated at 25° C. This DNA solution was sampled (5 μl each) at 30 second intervals and added to 100 μl of MB Nuclease Buffer which had been prepared in another tube. The mixture was incubated at 65° C. for 5 minutes to inactivate Exonuclease III and cooled down to 37° C. again. Then, 2 μl of Mung Bean Nuclease was added and the mixture was incubated at 37° C. for 30 minutes. After performing phenol extraction and ethanol precipitation, DNA was dissolved in 50 μl of Klenow Buffer, and 1 μl of Klenow Fragment was added. After the mixture was incubated at 37° C. for 15 minutes, thereby completely repairing the ends, 10 μl of the mixture was taken out and added to 100 μl of Ligation Solution A which had been prepared in another tube. Further, 12 μl of Ligation Solution B was added and stirred, and the mixture was reacted at 16° C. for 3 hours. Then, ethanol precipitation and rise were carried out. After the collected DNA was digested with a restriction enzyme XbaI for 1 hour, the mixture was added to a competent cell JM109 (100 μl), whereby transformation was carried out. Incidentally, the above-mentioned procedure was carried out by using, for example, Kilo-Sequence Deletion Kit (manufactured by Takara Co.) according to its protocol (FIG. 1).

2) Construction of a Recombinant Transfer Vector

The transformed *E. coli* was plated on a 2×TY plate containing kanamycin and cultured overnight at 37° C. The formed colonies were cultured overnight at 37° C. in 2×TY medium containing kanamycin. The plasmid DNA was extracted, digested with restriction enzymes BglII and BamHI and electrophoresed. It was confirmed that the DNA fragment was shortened, and a sequence analysis was performed, whereby the nucleotide sequence of the DNA fragment was confirmed. The plasmid DNA solution which was required for confirmation of the nucleotide sequence was digested with a restriction enzyme NotI, and inserted at the NotI site of a baculovirus transfer vector pVL1392 (manufactured by PHARMINGEN). A competent cell JM109 (100

µl) was transformed with this vector, plated on a 2×TY plate containing ampicillin and cultured overnight at 37° C. The formed colonies were cultured overnight at 37° C. in 2×TY medium containing ampicillin. The plasmid DNA was extracted, and a sequence analysis was performed. From the results of the analysis, the one in which the insert was inserted in the right direction was selected, which was used as a recombinant transfer vector pAcVP3(x)/EGFP (with the proviso that x represents the number of bases of the S4 cDNA encoding VP3 of BmCPV) (FIG. 2).

3) Construction of a Recombinant Baculovirus

A cultured insect cell Sf21 was cotransfected with the constructed recombinant transfer vector pAcVP3 (x)/EGFP (5 µg each) and a linear Baculogold Baculovirus DNA (0.5 µg) (manufactured by PHARMINGEN) according to the lipofectin method. Subsequently, the plaque was purified, whereby a recombinant virus AcVP3(x)/EGFP was constructed.

(3) Preparation of a Protein Complex Containing EGFP as a Target Protein

1) Expression of the Recombinant Protein in Sf21 Cell

As a control, double infection with AcVP3/GFP (Ikeda et al., (2001) J. Virol. 75, 988-995) and AcCP-H (Mori et al., (1993) J. Gen. Virol. 74, 99-102) or with AcVP3(XbaI)/GFP (International Application WO 02/36785A1) and AcCP-H, was performed. On the other hand, for the purpose of shortening VP3, double infection with AcVP3(x)/GFP and AcCP-H was performed. The double infection was performed at 10 p.f.u./cell for each case. After the virus was allowed to adsorb to cells at room temperature for 1 hour, the virus solution was removed, and 2 ml of TC-100 containing 10% fetal bovine calf serum was added, and the mixture was incubated at 27° C. for 4 days.

2) Purification of Polyhedra

The cubic polyhedra were collected from the infected cells on the 4th day. After washing with PBS (20 mM NaH2PO4, 20 mM Na2HPO4, 150 mM NaCl, pH7.2), the polyhedra were homogenized in ice with a homogenizer. The homogenate was washed with 1% Tween 20, and the polyhedra were collected by centrifugation. Then, centrifugation with the sucrose density gradient from 1.5 M to 2.2 M at 50,000×g for 45 minutes was performed to extract the fraction of polyhedra. The extracted sample was washed with PBS, followed by centrifugation at 15,000×g for 10 minutes, and purified polyhedra were collected.

3) Determination of Encapsulation of EGFP in a Polyhedron

Figure 3:
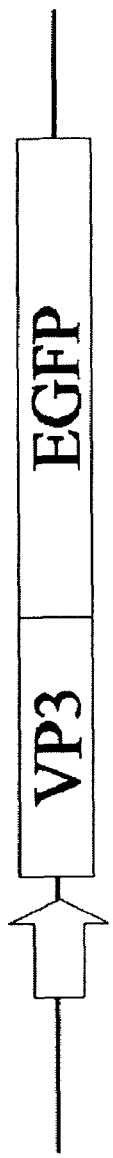
Figure 3:
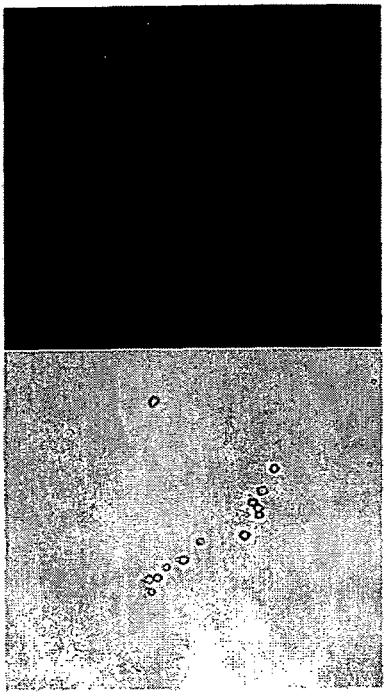
Figure 3:
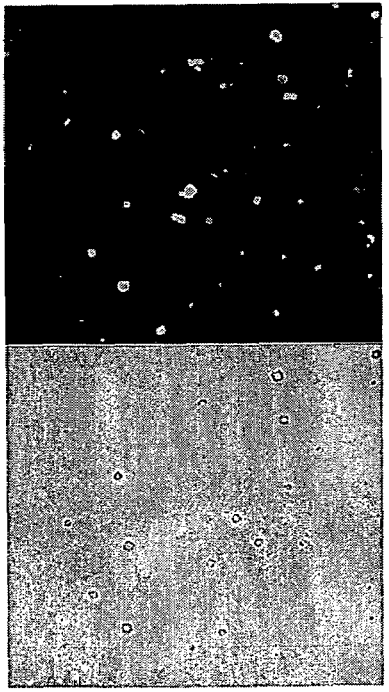

Polyhedra from cells subjected to double infection with AcVP3(X)/GFP and AcCP-H, and as a control, AcVP3/GFP and AcCP-H, and AcVP3(XbaI)/GFP and AcCP-H were purified, and encapsulation of EGFP in a polyhedron was determined based on the presence or absence of fluorescence from the polyhedron using a fluorescence microscope (manufactured by OLYMPUS-IX71) (FIG. 3). As a result, in any case, green fluorescence from the polyhedron was observed, and it was confirmed that VP3/GFP or VP3(XbaI)/GFP was encapsulated in the polyhedron.

Subsequently, for all AcVP3 (X)/GFP prepared as shown in FIG. 2, encapsulation of EGFP in the polyhedron was investigated. As a result, it was found that a VP3(250)/GFP molecule encoded by a chimeric gene in which a region containing from the 5'-terminus to the 250th base of the VP3 gene had been introduced into the 5'-terminus of the EGFP gene was embedded in the polyhedron. That is, it means that a signal for embedding a protein molecule specifically in the polyhedron (embedding signal for polyhedron) exists in a region up to the 79th amino acid residue at the N-terminus of VP3. Because of the existence of this signal, a VP3(250)/GFP molecule is encapsulated in the polyhedron, and as a result, green fluorescence from the polyhedron could be observed as shown in FIG. 3.

However, in the case of a chimeric gene in which a region containing from the 5'-terminus to the 130th base of the VP3 gene had been introduced into the 5'-terminus of the EGFP gene, a fusion GFP molecule VP3(130)/GFP encoded by this chimeric gene lost the function of being encapsulated in the polyhedron, and green fluorescence from the polyhedron was not observed at all (FIG. 3). This indicates that the embedding signal for polyhedron does not exist in the region up to the 39th amino acid residue at the N-terminus of VP3.

Further, a fragment from the 135th base to the 292nd base of VP3 was amplified by the PCR method, and a chimeric gene in which the amplified fragment was introduced into the 5'-terminus of the EGFP gene was constructed. As a result, a region encoding from the 41st amino acid residue at the N-terminus to the 93rd amino acid residue of VP3 is introduced into the N-terminus of EGFP. It was confirmed whether this VP3(135-292)/EGFP was encapsulated in the polyhedron in a similar manner, as a result, green fluorescence from the polyhedron was observed.

From the above result, for embedding of a protein molecule in a polyhedron via VP3, a very limited N-terminal region of VP3, that is, a region from the 41st amino acid residue at the N-terminus to the 79th amino acid residue of VP3 is found to function as an embedding signal for polyhedron.

Effect of Shortening of VP3

By introducing a gene encoding a region with different length from the 5'-terminus of the VP3 gene into the 5'-terminus of the GFP gene, regions of various amino acid sequences derived from VP3 were introduced into the N-terminus of GFP. The color development of green fluorescence by a fusion GFP molecule expressed from any of these chimeric genes was compared. As a result, as shown in FIG. 4, as the region of VP3 to be introduced into the N-terminus of GFP became shorter, the color development of green fluorescence was increased. However, in the case where the region was made shorter than the 79th amino acid residue from the N-terminus of VP3, the color development of green fluorescence was substantially the same. In this way, in the case where another amino acid sequence is introduced into a target protein, as the length of the sequence becomes shorter, the bioactivity of the target protein is increased. However, the sequence becomes shorter than necessary, the function as the signal will be lost.

The signal for encapsulating a target protein in the polyhedron of VP3 obtained in the present invention has a function sufficient for encapsulating the target protein in the polyhedron when it was introduced in the target protein molecule. Moreover, the signal has a length that does not disturb the bioactivity of the target protein. Further, it is indicated that by shortening the length of VP3 according to the present invention, a molecule which is larger by the length of VP3 that had been removed can be embedded in the polyhedron, therefore, the effect of the present invention is high.

Subsequently, according to the procedure of Example 1, a biosensor using a cubic protein complex about 10 µm on a side by applying human-derived Cyclin-dependent kinase (CDK5) as a target protein will be explained.

EXAMPLE 2

A biosensor was prepared by arranging a complex on a slide glass.

On a slide glass, 5 μl of a gelatin solution (gelatin: 0.5, Crk: 0.02) was dropped. Incidentally, Crk is chromium potassium sulfate (an antiseptic).

The front sides of the slide glass and a new slide glass were put together carefully. When the solution was spread therebetween, the slide glasses were slowly pulled apart. After the gelatin was completely dried, 1 μl of a complex solution which had been well stirred was dropped thereon, then dried, whereby a biosensor was prepared. This sensor was immersed in distilled water until use.

Incidentally, a complex solution represents a solution obtained by purifying a complex which has been expressed in a large amount in Sf21 cells, and suspending the purified complex in distilled water.

Verification

Verification method (1) Suppression of Peroxidase Activity

A hydrogen peroxide solution (adjusted to a final concentration of 1% by PBS) was placed on the part where the complex was dropped. After a 15-minute treatment at room temperature, washing was carried out with PBS (in order to remove the hydrogen peroxide solution).

In this way, the peroxidase activity to be a background was suppressed.

(2) Blocking with Normal Serum (5% NHS)

Normal horse serum was adjusted to a final concentration of 5% with PBS containing 0.3% Triton X-100 (T-PBS), and added to the slide glass. After a 20-minute treatment at room temperature, washing was carried out with T-PBS.

(3) Primary Antibody Reaction

An anti-Cdk5 monoclonal antibody was diluted to 100-fold with T-PBS containing 5% serum, and reaction was carried out at 37° C. for 3 hours. Then, washing was carried out with T-PBS.

(4) Biotinylated Anti-Mouse IgG Antibody Reaction

A biotinylated secondary antibody was diluted to 100-fold with T-PBS, and reaction was carried out at 37° C. for 1 hour. Then, washing was carried out with T-PBS.

On the other hand, A solution and B solution to be used in ABC reaction were diluted to 100-fold with T-PBS, and reaction was carried out for at least 30 minutes in advance.

(5) Reaction with ABC Reagent (VECTASTAIN ABC KIT STANDARD PK-6100)

After 1-hour reaction at room temperature, washing was carried out with T-PBS.

(6) Washing

Since precipitate is formed by the reaction of the subsequent DAB with phosphoric acid, in order to replace PBS, washing was carried out lightly with 50 mM Tris-HC (pH 7.5), and the solution was replaced.

(7) Incubation with DAB Substrate

DAB powder was added to 50 mM Tris-HCI solution at a concentration of 50 mg/ml, 16 μl of hydrogen peroxide solution was further added, and reaction was carried out at room temperature for 25 minutes. After the reaction, the slide glass was immersed in 50 mM Tris-HCI solution.

(8) Encapsulation with Glycerol/PBS

After the slide glass was dried, one drop of glycerol/PBS was dropped on the sample, then a cover glass was placed thereon avoiding any air bubble under.

Figure 5:
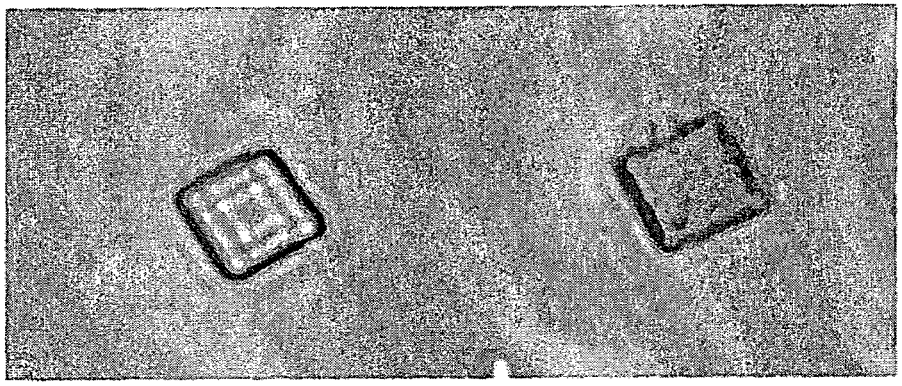
Figure 5:
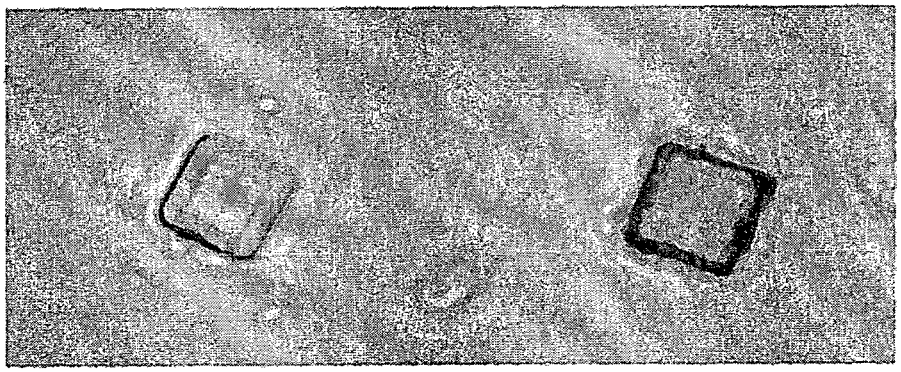

By using the above-mentioned verification method, an antigen-antibody reaction was attempted with a protein complex having a target protein encapsulated therein and a polyhedron without any protein encapsulated therein. The results are shown in FIG. 5. As shown in FIG. 5, as for the protein complex having Cdk5 encapsulated therein, the antigen-antibody reaction of the Cdk5 molecule and the anti-Cdk5 antibody could be observed on its surface. In this way, an antigen-antibody reaction, that is, a protein-to-protein interaction between an antigen protein and an antibody protein can be observed on the surface of a protein complex having a fused target protein encapsulated therein.

INDUSTRIAL APPLICABILITY

As described in detail above, according to the present invention, a protein complex comprising a polyhedral protein and a target protein can be efficiently produced by introducing a polyhedral protein, which is a constituent protein of a polyhedron having essentially an insect virus encapsulated therein and only a restricted region of a capsid protein VP3 of cytoplasmic polyhedrosis virus as a signal into a target protein.

In addition, a protein complex obtained by encapsulating a protein molecule having a bioactive function such as an enzymatic activity, an antigen-antibody reaction or a protein-to-protein interaction in a polyhedral protein can be used as an excellent biosensor or immobilized enzyme.

---

The invention claimed is:

1. An isolated protein complex comprising:
a polyhedral protein of *Bombyx mori* strain H cytoplasmic polyhedrosis virus (CPV) having *Bombyx mori* strain H CPV encapsulated therein; and
a target protein directly fused to the C-terminus of a fragment of a capsid protein VP3 of *Bombyx mori* strain H CPV,
wherein said fragment consists of the 41st to 79th amino acid residues of SEQ ID NO: 2 and is embedded in the polyhedral protein, and
wherein said target protein is heterologous with respect to said fragment and is encapsulated by the polyhedral protein.

2. The isolated protein complex according to claim 1, wherein the polyhedral protein has an effect on improvement in the stability of the target protein, protection thereof or improvement in the preservation property thereof, or a combination of any of these.

3. The isolated protein complex according to claim 1, wherein the target protein is at least one member selected from the group consisting of fluorescent or light-emitting proteins, enzymes, antigens, antibodies, cytokines, receptors and bioactive proteins.

4. A process for producing an isolated protein complex, comprising the steps of:
infecting a cell with a vector that has been integrated with a nucleic acid encoding a fragment of a capsid protein VP3 of *Bombyx mori* strain H cytoplasmic polyhedrosis virus (CPV) directly fused to a nucleic acid encoding a target protein together with a recombinant virus that has been integrated with a gene encoding a polyhedral protein of *Bombyx mori* strain H CPV, and
culturing the infected cell, whereby a protein complex comprising a polyhedral protein of *Bombyx mori* strain H CPV having *Bombyx mori* strain H CPV encapsulated therein and a target protein directly fused to the C-terminus of a fragment of a capsid protein VP3 of *Bombyx mori* strain H CPV is produced in the cell,
wherein the fragment of the produced protein complex consists of the 41st to 79th amino acid residues of SEQ ID NO: 2 and is embedded in the polyhedral protein, and
wherein said target protein is heterologous with respect to said fragment and is encapsulated by the polyhedral protein.

5. A biosensor comprising:
an isolated protein complex comprising:
a polyhedral protein of *Bombyx mori* strain H cytoplasmic polyhedrosis virus (CPV) having *Bombyx mori* strain H CPV encapsulated therein; and
a target protein directly fused to the C-terminus of a fragment of a capsid protein VP3 of *Bombyx mori* strain H CPV,
wherein said isolated protein complex is arranged in dots or lines on a substrate and immobilized thereon,
wherein the fragment consists of the 41st to 79th amino acid residues of SEQ ID NO: 2 and is embedded in the polyhedral protein, and
wherein said target protein is heterologous with respect to said fragment and is encapsulated by the polyhedral protein.

6. A biosensor according to claim 5, wherein said isolated protein complex is packed in such a manner that said isolated protein complex is to be contacted with a substance in a test solution in a recess formed on a substrate.

7. A biosensor according to claim 5, wherein said isolated protein complex is packed in a container in such a manner that said isolated protein complex is to be contacted with a substance in a test solution.

8. An isolated protein complex comprising:
a polyhedral protein of *Bombyx mori* strain H cytoplasmic polyhedrosis virus (CPV) having *Bombyx mori* strain H CPV encapsulated therein; and
a target protein directly fused to the C-terminus of a fragment of a capsid protein VP3 of *Bombyx mori* strain H CPV,
wherein said target protein is an enzyme, is heterologous with respect to said fragment, and is encapsulated by the polyhedral protein, and
wherein said fragment consists of the 41st to 79th amino acid residues of SEQ ID NO: 2 and is embedded in the polyhedral protein.

* * * * *

SEQUENCE LISTING

<160> NUMBER OF SEQ ID NOS: 2

<210> SEQ ID NO 1
<211> LENGTH: 3259
<212> TYPE: DNA
<213> ORGANISM: Bombyx mori cytoplasmic polyhedrosis virus (strain H)

<400> SEQUENCE: 1
agtaatttcc accatgtggc attatacgag tatcaacaat gacacgagag tagcacttga    60

```
ccccaaaccg aatcaaatta gaacgataac aaaaccaaac acagtacctc aactcggcac    120
agactatttg tatactttca actcacaacg acgatcacac acgttacgac tactagggcc    180
ttttcagtac ttcaacttct ccgagacaga tagaggacat ccattatttc gcctacctct    240
taagtatcca tcaaaagcaa taccagcaga tgagttaatt gacaatttac actcatggat    300
gcgttcagtt catctattac acgtacgctc ggaagacaac acgctacgtt acaactggat    360
gttaggtgtg tacgcgcgct caactaatta cactacacca gtcggacagt tggtagttaa    420
tgcgccagcg attctcaact attctaatcc gcaagatgca ttcaatagtg tatttgtagc    480
gttaggtata gactacattg atataccgat aactaacagc aacatctttg acgacagttc    540
gacaccctat aatgttcgta tttggcatgc ccctactatg acggaggtta accatatcct    600
tgcgctaatg cgaaagagta cactggtatc aacacattca tcttggcatt gggatgtatt    660
acatacgttt cactatagga gcgaatcaga tatgatcgat cactttgcgg ctaagatact    720
ggaagattgg cgacagaaag agaaacttga taagggcgca ttagtcgagg ctgatagagt    780
ggttcaaaga ctaataccat tgagctcttc aacatatgtg cagcgtttag cagcgatcgg    840
cgcgttatat cccaatgaat tcaccgagaa tgtattggac ttgagcagac tttcaacagc    900
attattgcaa ctatcagata cgtactatca acatgcaaat gatcaactca gacgtttata    960
tagacgtatg tataacgact caaggacgtt gtatatgaca caaagacatc aggagctact   1020
gctagcacaa ataactgccg atccgaatat acttttatat ccatatacat acatatttac   1080
aactgcgtat acttctatga actatatctc caatacaggg caaggccgta taaagcattc   1140
actagctgtt actggaacaa ctgagcatac tatagcagac ataacattgg gtccaatgag   1200
tgaggatgta gttaccatat ctatggtcga gccaatgagc atagctgcgg aggatatgta   1260
tggatacgtg cttgatacgc cgacacgtga catctggcca gcggacgaac agatagagca   1320
aaagggagac gcggtcgctt tgtatgatac aaaaacatct agagcactgg gcatgttcaa   1380
caacactgta cgtattgacg acttgttgtc tccgctatta ggcctggttt acagaacgta   1440
cattaaaggc gatacaatga ctatgaccca gggcagtttg gatcacctaa ctttatgtgc   1500
agcagttgat tcagacatca cttttgtggg taacaggatg atagcgccat ggcagagggg   1560
atatataccc aaagcgatgc atcggaataa ttcaacgatg aaaatgctca gtttatacgt   1620
ggcattgaaa aagttagaaa attttacaac caattcatat ctaatggctc cggatacatc   1680
cattatcttg ctcggtgcag agagagaacc cgctgtaagt atattgcgaa gatttaatcg   1740 tagcgttct aatgtacgca taatcggaat gggagacaga gcagtcgagc ctaacattag   1800
ggttcgtgtg ccattcccta tagataaaaa catctcggct gatttcatca tatgtgatat   1860
taactcctat gaggaccaga gttttgagtc catgttcggt gagactatat cggtagtgac   1920
tacatgcgct agcgccgcga cacgtgtact tgtgaagatt aatcatccat ctgaatatat   1980
gataaacagt gtaattgagc ggctatcaca attgggaggt gtgttttatc acactgcact   2040
actgaagaca gcttcgcaga acccatactc atacgaaaca tatatctaca ttacacctat   2100
agctgcggca gttaggttcc ccttttacag caactctgct ataattaata gatacatgac   2160
tgcagtggca gatgatgaga cgcctataat tcccagcatc catacagtta ttaaggggca   2220
tagtaacaca tactcacctg gtttgttctg tggatgtatt gacgtacaat cggcgccatt   2280
cgcactttca cagctaaaat cctattgctc agaagcgaca acctggcgcg ttgacagtga   2340
cgataactta gttaacatca ttgccagaat tgatcccgcg cgtatagctt tggaatttcg   2400
aacacgctca aatactagcg cctatcatga ataccaacgc tatgtaccaa atggactcgg   2460
```

-continued

```
ctttaaaggg cggaagacgc gagagtttag gtatatacat cgtgaggtaa catttataca    2520
taaactgatg acatatgctt taatacgaga gcagatatca ttaactgaaa acatgactca    2580
agtggtaagt attggcggcc gtaacctcgc tgatatatct gtcgtccctc ttaatatgaa    2640
atacgtggtg atagacccag ccacacgtat cgaaacgtta acgcaggaaa agaagaatat    2700
tgaagtacaa tctagaccat tctcatttga tgcggcaagc atggatttag agaataattc    2760
tatatatcta tttatcgcag taatcatgaa tgaaccaaat ggagcagcta ctcccgccag    2820
aacgcaaatg gataagatac gtaatgttgc cacagctatg ctaaccagga ctaactgcgt    2880
cgcatacatt tcgttttacg aggcagggat aatcacaaga ttggatcaat caaccgcgca    2940
taagactata cgtgttgaag aaggtcgact gaaagtggca aattatgtac ccgtggatac    3000
gctcgttgaa gcagacgtga cgttgatgtt acgcgatatc ggcataacac atgagataat    3060
aagaccatcg acgcctgaac tcataaatgc ctgttcaaac tatggcattc gcctaggttc    3120
gacaggtggc gcggttttgg acgtgttcaa tcactactct cccgtgatca aacttgtacg    3180
ctcgtaatgc tgagtcttaa ccacaggagt tgaggagctc tgtcccggga gggacactgt    3240
ggggtgggaa acgttagcc                                                 3259
```

<210> SEQ ID NO 2
<211> LENGTH: 1057
<212> TYPE: PRT
<213> ORGANISM: Bombyx mori cytoplasmic polyhedrosis virus (strain H)

<400> SEQUENCE: 2

```
Met Trp His Tyr Thr Ser Ile Asn Asn Asp Thr Arg Val Ala Leu Asp
1               5                   10                  15

Pro Lys Pro Asn Gln Ile Arg Thr Ile Thr Lys Pro Asn Thr Val Pro
            20                  25                  30

Gln Leu Gly Thr Asp Tyr Leu Tyr Thr Phe Asn Ser Gln Arg Arg Ser
        35                  40                  45

His Thr Leu Arg Leu Leu Gly Pro Phe Gln Tyr Phe Asn Phe Ser Glu
    50                  55                  60

Thr Asp Arg Gly His Pro Leu Phe Arg Leu Pro Leu Lys Tyr Pro Ser
65                  70                  75                  80

Lys Ala Ile Pro Ala Asp Glu Leu Ile Asp Asn Leu His Ser Trp Met
                85                  90                  95

Arg Ser Val His Leu Leu His Val Arg Ser Glu Asp Asn Thr Leu Arg
            100                 105                 110

Tyr Asn Trp Met Leu Gly Val Tyr Ala Arg Ser Thr Asn Tyr Thr Thr
        115                 120                 125

Pro Val Gly Gln Leu Val Val Asn Ala Pro Ala Ile Leu Asn Tyr Ser
    130                 135                 140

Asn Pro Gln Asp Ala Phe Asn Ser Val Phe Val Ala Leu Gly Ile Asp
145                 150                 155                 160

Tyr Ile Asp Ile Pro Ile Thr Asn Ser Asn Ile Phe Asp Asp Ser Ser
                165                 170                 175

Thr Pro Tyr Asn Val Arg Ile Trp His Ala Pro Thr Met Thr Glu Val
            180                 185                 190

Asn His Ile Leu Ala Leu Met Arg Lys Ser Thr Leu Val Ser Thr His
        195                 200                 205

Ser Ser Trp His Trp Asp Val Leu His Thr Phe His Tyr Arg Ser Glu
    210                 215                 220
```

-continued

Ser Asp Met Ile Asp His Phe Ala Ala Lys Ile Leu Glu Asp Trp Arg
225                 230                 235                 240

Gln Lys Glu Lys Leu Asp Lys Gly Ala Leu Val Glu Ala Asp Arg Val
            245                 250                 255

Val Gln Arg Leu Ile Pro Leu Ser Ser Thr Tyr Val Gln Arg Leu
        260                 265                 270

Ala Ala Ile Gly Ala Leu Tyr Pro Asn Glu Phe Thr Glu Asn Val Leu
        275                 280                 285

Asp Leu Ser Arg Leu Ser Thr Ala Leu Leu Gln Leu Ser Asp Thr Tyr
    290                 295                 300

Tyr Gln His Ala Asn Asp Gln Leu Arg Arg Leu Tyr Arg Met Tyr
305                 310                 315                 320

Asn Asp Ser Arg Thr Leu Tyr Met Thr Gln Arg His Gln Glu Leu Leu
                325                 330                 335

Leu Ala Gln Ile Thr Ala Asp Pro Asn Ile Leu Leu Tyr Pro Tyr Thr
            340                 345                 350

Tyr Ile Phe Thr Thr Ala Tyr Thr Ser Met Asn Tyr Ile Ser Asn Thr
        355                 360                 365

Gly Gln Gly Arg Ile Lys His Ser Leu Ala Val Thr Gly Thr Thr Glu
    370                 375                 380

His Thr Ile Ala Asp Ile Thr Leu Gly Pro Met Ser Glu Asp Val Val
385                 390                 395                 400

Thr Ile Ser Met Val Glu Pro Met Ser Ile Ala Ala Glu Asp Met Tyr
                405                 410                 415

Gly Tyr Val Leu Asp Thr Pro Thr Arg Asp Ile Trp Pro Ala Asp Glu
            420                 425                 430

Gln Ile Glu Gln Lys Gly Asp Ala Val Ala Leu Tyr Asp Thr Lys Thr
        435                 440                 445

Ser Arg Ala Leu Gly Met Phe Asn Asn Thr Val Arg Ile Asp Asp Leu
450                 455                 460

Leu Ser Pro Leu Leu Gly Leu Val Tyr Arg Thr Tyr Ile Lys Gly Asp
465                 470                 475                 480

Thr Met Thr Met Thr Gln Gly Ser Leu Asp His Leu Thr Leu Cys Ala
                485                 490                 495

Ala Val Asp Ser Asp Ile Thr Phe Val Gly Asn Arg Met Ile Ala Pro
            500                 505                 510

Leu Ala Glu Gly Tyr Ile Pro Lys Ala Met His Arg Asn Asn Ser Thr
        515                 520                 525

Met Lys Met Leu Ser Leu Tyr Val Ala Leu Lys Lys Leu Glu Asn Phe
    530                 535                 540

Thr Thr Asn Ser Tyr Leu Met Ala Pro Asp Thr Ser Ile Ile Leu Leu
545                 550                 555                 560

Gly Ala Glu Arg Glu Pro Ala Val Ser Ile Leu Arg Arg Phe Asn Arg
                565                 570                 575

Ser Val Ser Asn Val Arg Ile Ile Gly Met Gly Asp Arg Ala Val Glu
            580                 585                 590

Pro Asn Ile Arg Val Arg Val Pro Phe Pro Ile Asp Lys Asn Ile Ser
        595                 600                 605

Ala Asp Phe Ile Ile Cys Asp Ile Asn Ser Tyr Glu Asp Gln Ser Phe
    610                 615                 620

Glu Ser Met Phe Gly Glu Thr Ile Ser Val Val Thr Thr Cys Ala Ser
625                 630                 635                 640

Ala Ala Thr Arg Val Leu Val Lys Ile Asn His Pro Ser Glu Tyr Met

-continued

```
                645                 650                 655
Ile Asn Ser Val Ile Glu Arg Leu Ser Gln Leu Gly Gly Val Phe Tyr
                660                 665                 670

His Thr Ala Leu Leu Lys Thr Ala Ser Gln Asn Pro Tyr Ser Tyr Glu
                675                 680                 685

Thr Tyr Ile Tyr Ile Thr Pro Ile Ala Ala Val Arg Phe Pro Phe
                690                 695                 700

Tyr Ser Asn Ser Ala Ile Ile Asn Arg Tyr Met Thr Ala Val Ala Asp
705                 710                 715                 720

Asp Glu Thr Pro Ile Pro Ser Ile His Thr Val Ile Lys Gly His
                725                 730                 735

Ser Asn Thr Tyr Ser Pro Gly Leu Phe Cys Gly Cys Ile Asp Val Gln
                740                 745                 750

Ser Ala Pro Phe Ala Leu Ser Gln Leu Lys Ser Tyr Cys Ser Glu Ala
                755                 760                 765

Thr Thr Trp Arg Val Asp Ser Asp Asn Leu Val Asn Ile Ile Ala
                770                 775                 780

Arg Ile Asp Pro Ala Arg Ile Ala Leu Glu Phe Arg Thr Arg Ser Asn
785                 790                 795                 800

Thr Ser Ala Tyr His Glu Tyr Gln Arg Tyr Val Pro Asn Gly Leu Gly
                805                 810                 815

Phe Lys Gly Arg Lys Thr Arg Glu Phe Arg Tyr Ile His Arg Glu Val
                820                 825                 830

Thr Phe Ile His Lys Leu Met Thr Tyr Ala Leu Ile Arg Glu Gln Ile
                835                 840                 845

Ser Leu Thr Glu Asn Met Thr Gln Val Val Ser Ile Gly Gly Arg Asn
                850                 855                 860

Leu Ala Asp Ile Ser Val Val Pro Leu Asn Met Lys Tyr Val Val Ile
865                 870                 875                 880

Asp Pro Ala Thr Arg Ile Glu Thr Leu Thr Gln Glu Lys Lys Asn Ile
                885                 890                 895

Glu Val Gln Ser Arg Pro Phe Ser Phe Asp Ala Ala Ser Met Asp Leu
                900                 905                 910

Glu Asn Asn Ser Ile Tyr Leu Phe Ile Ala Val Ile Met Asn Glu Pro
                915                 920                 925

Asn Gly Ala Ala Thr Pro Ala Arg Thr Gln Met Asp Lys Ile Arg Asn
                930                 935                 940

Val Ala Thr Ala Met Leu Thr Arg Thr Asn Cys Val Ala Tyr Ile Ser
945                 950                 955                 960

Phe Tyr Glu Ala Gly Ile Ile Thr Arg Leu Asp Gln Ser Thr Ala His
                965                 970                 975

Lys Thr Ile Arg Val Glu Glu Gly Arg Leu Lys Val Ala Asn Tyr Val
                980                 985                 990

Pro Val Asp Thr Leu Val Glu Ala Asp Val Thr Leu Met Leu Arg Asp
                995                 1000                1005

Ile Gly Ile Thr His Glu Ile Ile Arg Pro Ser Thr Pro Glu Leu
                1010                1015                1020

Ile Asn Ala Cys Ser Asn Tyr Gly Ile Arg Leu Gly Ser Thr Gly
                1025                1030                1035
```

-continued

```
Gly Ala Val Leu Asp Val Phe Asn His Tyr Ser Pro Val Ile Lys
    1040            1045            1050

Leu Val Arg Ser
    1055
```